United States Patent
Saalbach et al.

(10) Patent No.: US 10,402,967 B2
(45) Date of Patent: Sep. 3, 2019

(54) DEVICE, SYSTEM AND METHOD FOR QUALITY ASSESSMENT OF MEDICAL IMAGES

(71) Applicant: KONINKLIJKE PHILIPS N.V., Eindhoven (NL)

(72) Inventors: Axel Saalbach, Hamburg (DE); Daniel Bystrov, Hamburg (DE); Thomas Buelow, Hamburg (DE); Kongkuo Lu, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 64 days.

(21) Appl. No.: 15/378,112

(22) Filed: Dec. 14, 2016

(65) Prior Publication Data
US 2017/0178320 A1    Jun. 22, 2017

Related U.S. Application Data

(60) Provisional application No. 62/270,191, filed on Dec. 21, 2015.

(30) Foreign Application Priority Data

Dec. 22, 2015  (EP) .................................... 15201919

(51) Int. Cl.
*G06K 9/00* (2006.01)
*G06T 7/00* (2017.01)
(Continued)

(52) U.S. Cl.
CPC .......... *G06T 7/0012* (2013.01); *G06F 19/321* (2013.01); *G06T 1/0007* (2013.01);
(Continued)

(58) Field of Classification Search
CPC ....... G06T 7/0012; G06T 7/33; G06T 7/0002; G06T 7/174; G06T 7/0014; G06T 1/0007; G06T 19/20; G06T 2207/10132; G06T 2207/30168; G06T 2207/00; G06T 2207/20004; G06T 2207/30004;
(Continued)

(56) References Cited

U.S. PATENT DOCUMENTS 5,740,267 A * 4/1998 Echerer .................. G06T 5/009 382/132
8,824,752 B1 * 9/2014 Fonte .................... G06T 7/0012 382/126

(Continued)

*Primary Examiner* — Jose L Couso

(57) ABSTRACT

The present invention relates to a device, system and method for quality assessment of medical images. The device comprises an image input configured to obtain a medical image acquired according to an imaging guideline, a database access unit configured to access a database storing reference images for a plurality of imaging guidelines and for obtaining a reference image based on the imaging guideline used for acquisition of the obtained medical image, an analysis unit configured to analyze the obtained medical image in view of the obtained reference image and/or the used imaging guideline to generate quality information representing the quality of the obtained medical image, and a quality output configured to output the generated quality information.

14 Claims, 2 Drawing Sheets

(51) Int. Cl.
*G06T 1/00* (2006.01)
*G06F 19/00* (2018.01)

(52) U.S. Cl.
CPC .. *G06T 7/0014* (2013.01); *G06T 2207/10004* (2013.01); *G06T 2207/30168* (2013.01)

(58) Field of Classification Search
CPC ....... G06T 2207/20081; G06T 2210/41; A61B 8/0866; A61B 8/461; A61B 8/467; A61B 8/469; A61B 8/5215; A61B 8/5223; A61B 6/5211; A61B 6/5217; A61B 6/48; A61B 6/5294; A61B 2576/00; A61B 2505/00; A61B 5/00; A61B 5/743; G06F 19/321; G06F 19/26; G06F 19/28; G06F 19/30; G06F 19/324; G06F 19/325; G06F 19/3418; G16H 15/00; G16H 50/20; G16H 50/30; G16H 50/50; G16H 30/20; G16H 40/20; G06K 2009/057; A61N 5/103; A61N 2005/0626; G06Q 50/24
See application file for complete search history.

(56) References Cited

U.S. PATENT DOCUMENTS

| | | | | |
|---|---|---|---|---|
| 10,102,348 | B2* | 10/2018 | Vendrell | G16H 50/30 715/771 |
| 2004/0029213 | A1* | 2/2004 | Callahan | G01N 15/1475 430/40.5 |
| 2006/0052690 | A1* | 3/2006 | Sirohey | A61B 6/481 600/420 |
| 2008/0226148 | A1* | 9/2008 | Gu | G06T 5/007 382/128 |
| 2009/0028403 | A1* | 1/2009 | Bar-Aviv | G06F 19/321 382/128 |
| 2009/0228299 | A1* | 9/2009 | Kangarloo | G06F 19/321 705/2 |
| 2009/0274384 | A1* | 11/2009 | Jakobovits | G06F 19/321 382/254 |
| 2010/0172567 | A1* | 7/2010 | Prokoski | A61B 5/0064 382/132 |
| 2011/0110572 | A1* | 5/2011 | Guehring | A61B 6/5258 382/131 |
| 2011/0188718 | A1* | 8/2011 | Hill | G06F 19/321 382/128 |
| 2013/0085774 | A1* | 4/2013 | Chen | G09B 23/28 705/2 |
| 2013/0190600 | A1* | 7/2013 | Gupta | A61B 8/0866 600/410 |
| 2013/0326386 | A1* | 12/2013 | Vendrell | G06F 19/321 715/771 |
| 2014/0219500 | A1* | 8/2014 | Moehrle | G06F 19/321 382/103 |
| 2014/0316770 | A1* | 10/2014 | Sevenster | G06F 17/21 704/9 |
| 2015/0065803 | A1* | 3/2015 | Douglas | A61B 1/00009 600/200 |
| 2016/0110584 | A1* | 4/2016 | Remiszewski | G06T 7/0012 382/133 |
| 2016/0155236 | A1* | 6/2016 | Davey | G06T 19/20 382/131 |
| 2016/0259992 | A1* | 9/2016 | Knodt | G06K 9/6201 |
| 2016/0283657 | A1* | 9/2016 | Bhotika | G06F 19/321 |
| 2017/0038951 | A1* | 2/2017 | Reicher | G06F 19/321 |
| 2017/0053064 | A1* | 2/2017 | Bhavani | G06Q 50/22 |
| 2017/0103173 | A1* | 4/2017 | Vilsmeier | G06F 19/345 |

* cited by examiner

DEVICE, SYSTEM AND METHOD FOR QUALITY ASSESSMENT OF MEDICAL IMAGES

FIELD OF THE INVENTION

The present invention relates to a device, system and method for quality assessment of medical images.

BACKGROUND OF THE INVENTION

Worldwide there is an increased pressure on imaging departments to measure and improve the quality of care. In the United States, this is driven by regulatory agencies, the Centers for Medicare and Medicaid Services (CMS), payers as well as professional societies.

Common key performance indicators (KPIs) are based on quantities such as equipment utilization, idle time or patient throughput. By now, even first benchmarks for quality improvement became available which allow for a comparison between different sites. Most of the KPIs are derived from device logs or clinical information systems (i.e. non-image data).

Next to non-image data, the images themselves provide a broad range of options to define meaningful quality metrics. One example is the adherence to guidelines. Imaging departments typically define scan planning and/or patient positioning guidelines which are used by the technician in order to plan the geometry of a scan. These guidelines ensure that the anatomy of interest is completely covered and that an unnecessary dose exposure is avoided. Incorrect scans can reduce the diagnostic value of an image, and can make a re-scan necessary.

Another (even more fundamental) issue is the correctness of anatomical information. While the Digital Imaging and Communications in Medicine (DICOM) standard provides multiple options to indicate the scanned anatomy (e.g. Body Part Examined value or Anatomic Region Sequence code), this information is not reliable. Errors in the anatomical information could have a negative impact on the clinical workflow, as e.g. relevant prior scans are more difficult to identify. Furthermore, it makes a statistical evaluation of the performed scans in a department impossible.

SUMMARY OF THE INVENTION

It is an object of the present invention to provide a device, system and method for improved quality assessment of medical images, in particular for easy and fast assessment of the correctness of anatomical information depicted in an acquired medical image.

In a first aspect of the present invention a device for quality assessment of medical images is presented comprising:
an image input configured to obtain a medical image acquired according to an imaging guideline,
a database access unit configured to access a database storing reference images for a plurality of imaging guidelines and for obtaining a reference image based on the imaging guideline used for acquisition of the obtained medical image,
an analysis unit configured to analyze the obtained medical image in view of the obtained reference image and/or the used imaging guideline to generate quality information representing the quality of the obtained medical image, and
a quality output configured to output the generated quality information.

In a further aspect of the present invention a method for quality assessment of medical images is presented comprising:
obtaining a medical image acquired according to an imaging guideline,
accessing a database storing reference images for a plurality of imaging guidelines and for obtaining a reference image based on the imaging guideline used for acquisition of the obtained medical image,
analyzing the obtained medical image in view of the obtained reference image and/or the used imaging guideline to generate quality information representing the quality of the obtained medical image, and
outputting the generated quality information.

In still a further aspect of the present invention a system for quality assessment of medical images is presented comprising:
an image acquisition device configured to acquire medical images of a subject according to an imaging guideline, and
a device as disclosed herein for quality assessment of medical images acquired with said imaging guideline.

In still a further aspect of the present invention a quality assessment system is presented comprising a processor and a computer-readable storage medium, wherein the computer-readable storage medium contains instructions for execution by the processor, wherein the instructions cause the processor to perform the steps of:
obtaining a medical image acquired according to an imaging guideline,
accessing a database storing reference images for a plurality of imaging guidelines and for obtaining a reference image based on the imaging guideline used for acquisition of the obtained medical image,
analyzing the obtained medical image in view of the obtained reference image and/or the used imaging guideline to generate quality information representing the quality of the obtained medical image, and
outputting the generated quality information.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

It shall be understood that the claimed method, systems, computer program and medium have similar and/or identical preferred embodiments as the claimed device, in particular as defined in the dependent claims and as disclosed herein.

The present invention provides an automated approach based on image processing techniques since a manual evaluation of a large set of images with respect to these criteria is prohibitive. The presented technique allows not only for analysis of a single medical image, but allows for (retrospective) analysis of large image archives in order to derive meaningful quality information (quality indicators) from the image data itself. Amongst others, these criteria may relate to the percentage of correctly planned scans and percentage of correctly annotated images.

In order to compute these quantities, image processing techniques are employed to analyze the content of available medical images. The findings are compared with one or more available or obtained reference images, e.g. with available DICOM information or one or more Atlas images, and/or with an imaging guideline, such as an imaging (or image acquisition) protocol, available scan planning guidelines, a DICOM protocol, clinical guidelines, etc., in order to derive quality information, e.g. KPI values.

The present invention is not limited to the use of a single medical image in the quality assessment and analysis. In some applications two or more medical images are evaluated and analyzed as a set. For instance, in mammography, a joint quality assessment and analysis of a pair of medical images may be performed.

In an embodiment said analysis unit is further configured to compare the obtained medical image with the reference image to generate quality information representing a level of similarity. This provides a simple way of obtaining quality information using only image comparison techniques.

In another embodiment said analysis unit is further configured to check compliance of the obtained medical image with the used imaging guideline to generate quality information representing compliance and/or the level of compliance. This provides another way of obtaining quality information in a simple manner. A further improvement may be obtained by using both the reference image and the imaging guideline for the assessment.

The analysis unit may further be configured to use an imaging guideline including attributes, in particular DICOM attributes, and/or imaging planning guidelines in the analysis to generate said quality information representing compliance and/or the level of compliance of the obtained medical image with the attributes and/or imaging planning guidelines. This further improves the reliability of the assessment.

In another embodiment the device further comprises an image processing unit configured to detect target anatomy and/or anatomical landmarks in the obtained medical image, wherein said analysis unit is further configured to compare the detected target anatomy and/or anatomical landmarks in the obtained medical image with target anatomy and/or anatomical landmarks in the reference image to generate quality information representing a level of similarity. The use of target anatomy and/or anatomical landmarks allows a precise analysis and assessment.

The device may further comprise a registration unit configured to perform registration of the obtained medical image with the reference image, wherein said analysis unit is configured to use the registered medical image in the analysis. Thus, misinterpretations and wrong quality assessments may be avoided due to wrong comparisons because of non-registered images. Further, the registration may be used to check the compliance of the obtained medical image with the requirements.

Still further, the device may further comprise an evaluation unit configured to evaluate the generated quality information of the quality assessment of a plurality of medical images to obtain an evaluation result, wherein said output unit is further configured to output said evaluation result. Said evaluation result may e.g. be training information or guidance information used for training or guidance of medical personnel to improve the future acquisition of medical images.

The device may further comprise a converter configured to convert a textual description of the imaging guideline into a reference image. In another embodiment the converter converts a textual description of the imaging guideline into standard text as used by a database linking standard text with reference images, wherein said database access unit is configured to retrieve a reference image from said database. Thus, a reference image needs not to be available as such, but may also be generated or retrieved from the imaging guideline, e.g. a textual description.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
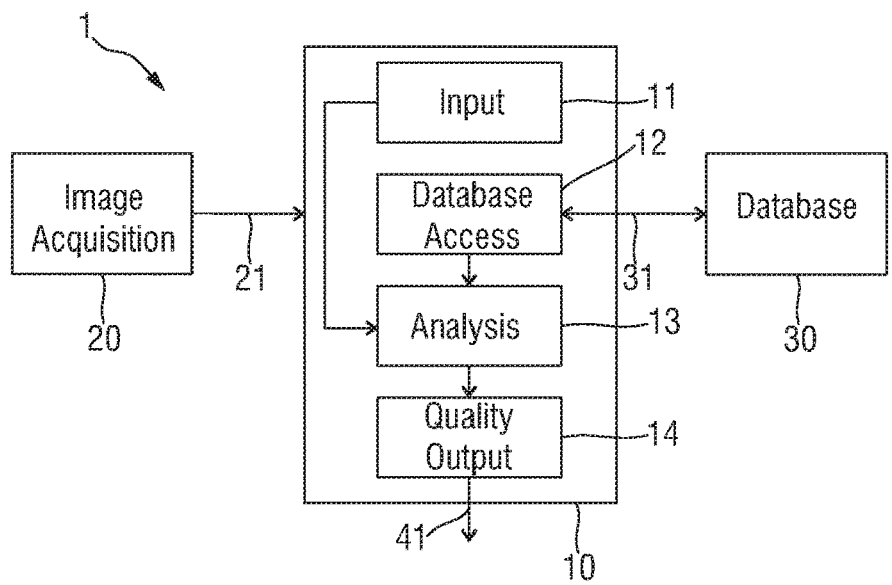
FIG. 1 shows a schematic diagram of an embodiment of a system and device for quality assessment of medical images according to the present invention.

FIG. 1 shows a schematic diagram of an embodiment of a system 1 and device 10 for quality assessment of medical images according to the present invention. In addition to the device 10 the system comprises an image acquisition device 20 configured to acquire medical images of a subject according to an imaging guideline. The image acquisition device 20 may generally be of any kind, which allows acquisition of a medical image, such as an x-ray device, a CT device, an ultrasound device, an MR device, a PET device, a SPECT device, etc.

Based on the image data, which may e.g. a single image, a set of images, a two- or three-dimensional image data set, etc., the device 10 assesses their quality acquired with said image acquisition device 20 according to an imaging guideline. Such an imaging guideline may be prescribed by a manual of the imaging guideline, or by a guideline, by a standard, by a physician, etc. and defines which kind if image data shall be acquired. For instance, an imaging guideline may define that a x-ray projection image of the subject's torso from the front side shall be acquired.

The device 10 comprises an image input 11 configured to obtain a medical image 21 acquired according to an imaging guideline. The image input 11 may e.g. be a data interface connected to the image acquisition unit 20 or an image buffer or an image database to obtain, i.e. receive or retrieve, medical image data 21 of the subject acquired with the image acquisition unit 20. The image data may be obtained by the image input 11 in a wired or wireless manner.

The device 10 further comprises a database access unit 12 configured to access a database 30 storing reference images for a plurality of imaging guidelines and for obtaining a reference image 31 based on the imaging guideline used for acquisition of the obtained medical image. The database access unit 12 may e.g. be another data interface for accessing a database 30, e.g. a hospital archive, an online archive, an Atlas database, etc.

The device 10 further comprises an analysis unit 13 configured to analyze the obtained medical image 21 in view of the obtained reference image 31 and/or the used imaging guideline to generate quality information 41 representing the quality of the obtained medical image 21. The analysis unit may e.g. be software or hardware unit, e.g. an FPGA, or a processor or computer programmed accordingly.

The generated quality information 41 is output by a quality output 14, e.g. an output interface for transmitting the generated quality information 41 to another entity (e.g. a hospital workstation or another computer for storage or further processing) or a display for displaying the generated quality information.

Figure 2:
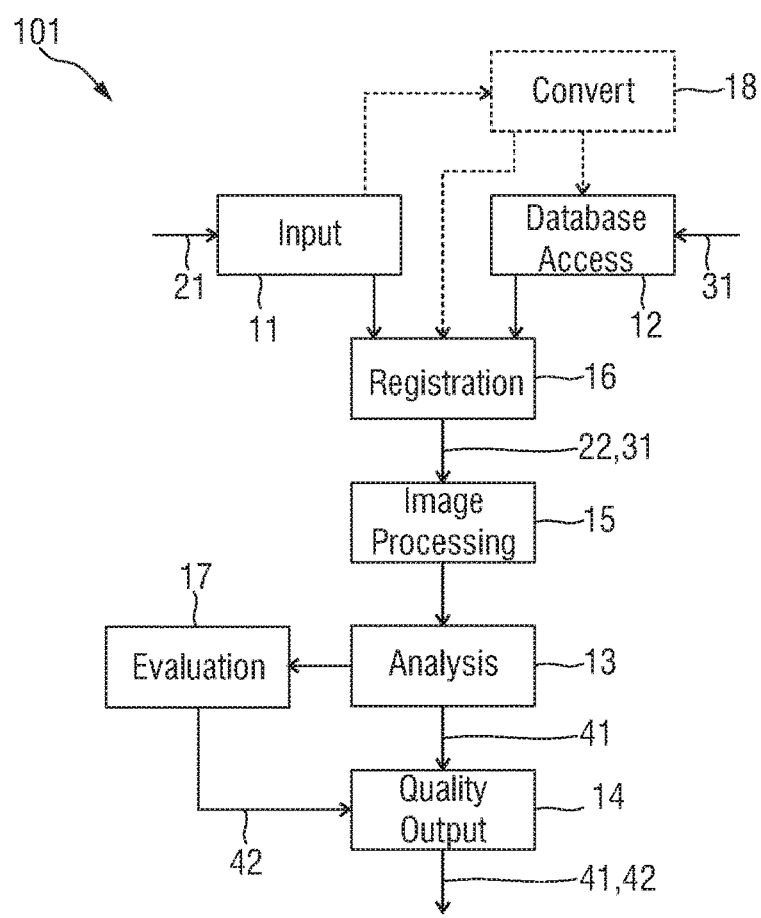
FIG. 2 shows a schematic diagram of another embodiment of a device according to the present invention.

FIG. 2 shows a schematic diagram of another embodiment of a device 10' according to the present invention. In this embodiment the device 10' comprises one or more of the following components.

An image processing unit 15 may be provided which is configured to detect target anatomy and/or anatomical landmarks in the obtained medical image 21. The analysis unit 13 may then compare the detected target anatomy and/or anatomical landmarks in the obtained medical image 21 with target anatomy and/or anatomical landmarks in the reference image 31 to generate quality information 41 representing a level of similarity. A possible implementation may e.g. use specific landmark detectors in order to identify these landmarks in the actual image, and compute the difference to the actual field of view.

Alternatively or in addition, a registration unit 16 may be provided which is configured to perform registration of the obtained medical image 21 with the reference image 31. In an embodiment landmarks (detected in the obtained image 21 and obtained or known in the reference image 31) may be used for the registration. The analysis unit 13 may then be configured to use the registered medical image 22 in the analysis, e.g. by computing the difference of the field of view (FOV) of the obtained image 21 and the FOV of the reference image 31.

In a practical scenario it is of relevance if the relevant details are covered in the FOV and if the margins are not too large (e.g. in order to avoid excessive dose in CT). This may be expressed in e.g. landmark deviation in cm or in a qualitative statement (e.g. arms up instead of arms down).

Alternatively or in addition, an evaluation unit 17 may be provided which is configured to evaluate the generated quality information 41 of the quality assessment of a plurality of medical images to obtain an evaluation result 42. The output unit 14 may then be further configured to output said evaluation result 42. Hereby, the evaluation unit may be configured to generate guidance information indicating suggestions for improvement of future image acquisition.

A practical embodiment of the device would be a dedicated reporting solution or reporting tool, which can be installed in a clinical department. In such an embodiment the proposed system may comprise a database access unit 13 for connecting to a Picture Archiving and Communication System (PACS) via a DICOM protocol. An image processing unit 15 allows for the detection of the target anatomy/anatomical landmarks. The analysis unit 13 compares the outcome of the image processing unit 15 with the DICOM data or existing guidelines. A database unit may be provided for storing information about the extracted DICOM data, the detected anatomical structures and the results of the analysis unit 13. Finally, a reporting solution (representing the output unit 14) is provided for the visualization and analysis of the results. Furthermore, the proposed invention may also be embedded in an imaging device or system, e.g. directly on the scanner, or on a PACS or on any other DICOM network node.

The database access unit 13 (also called data extraction module) preferably provides access to all relevant DICOM images from the archive. Using the image processing unit, which can be implemented via e.g. atlas based registration or classification based approaches, the target anatomy in the field of view can be identified. Given these information, the correctness of the DICOM attributes can be verified. Additionally, the compliance with respect to planning guidelines can be assessed (e.g. by evaluating the visibility of specific landmarks and their distance to the image borders). The results of this analysis can statistically be evaluated and reported. For instance, the percentage of correctly planned thorax scans can be evaluated. The results of this analysis can be used as an input for an intelligent data repository/a reporting solution. In this way, e.g. the number of thorax scans can be assessed which were planned correctly (at the level of individual technicians). The reporting solution can link the detected quality issues with known possible root causes. From these root causes and the detected frequency of the related quality issue, suggestions for future quality improvement actions, e.g. training of technologists, can be derived.

The imaging guideline may e.g. be a clinical guideline, based e.g. on a textual description. For instance, for an abdomen scan an image acquisition protocol may say "Dome of diaphragm to iliac crest". In an embodiment the textual description may be used to obtain a reference image which is then used in the analysis. For instance, the textual description may be converted, by an optional converter 18, into a reference image.

In another embodiment the converter 18 may be used to convert the textual description into standard text as used by a standard database linking standard text with reference images. Thus, the obtained standard text may then be used by the database access unit 12 to retrieve a reference image from such a standard database.

Figure 3:
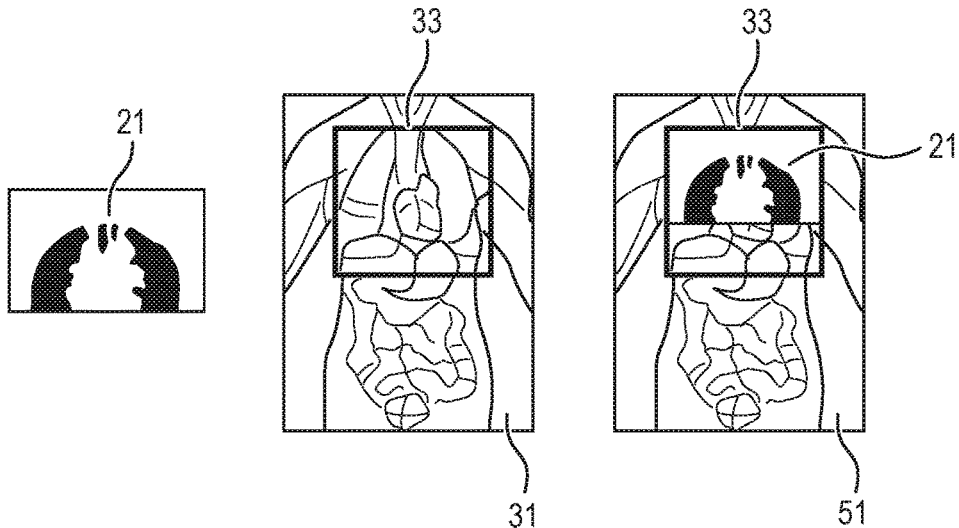
FIG. 3 shows a diagram illustrating an example of the proposed method.

FIG. 3 shows a diagram illustrating an example of the proposed method. An obtained medical image 21 is compared to a reference image 31, in which a frame 33 indicates the area that should be covered according to the imaging guideline, e.g. a thorax plan. In a combined image 51 the frame 33 and the area of the obtained medical image 21 are shown, so that it can be seen that there is an overlap of less than 80%. This means that the thorax plan is erroneous because the coverage is less than 80%, which would be issued as quality information for this case.

Generally, the overlap may be compared to user defined or predetermined threshold (e.g. for DICOM anatomy information validation). With respect to image quality, landmark distances and/or the presence landmarks may be checked additionally or instead. Further, this overlap may be compared to site specific guidelines.

Figure 4:
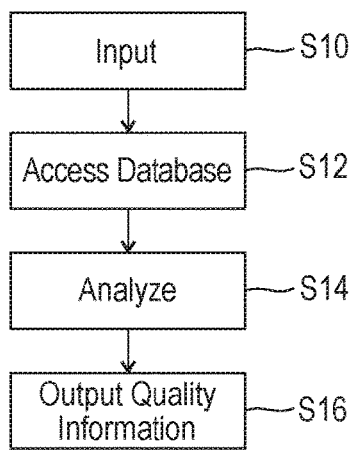
FIG. 4 shows a flowchart of an embodiment of a method for quality assessment of medical images according to the present invention.

FIG. 4 shows a flowchart of an embodiment of a method 100 for quality assessment of medical images according to the present invention. In a first step S10 a medical image is acquired according to an imaging guideline. In a second step S12 a database storing reference images for a plurality of imaging guidelines is accessed and a reference image is obtained based on the imaging guideline used for acquisition of the obtained medical image. In a third step S14 the obtained medical image is analyzed in view of the obtained reference image and/or the used imaging guideline to generate quality information representing the quality of the obtained medical image. In a fourth step S16 the generated quality information is output.

Figure 5:
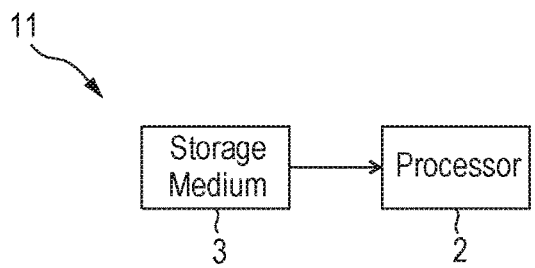
FIG. 5 shows a schematic diagram of another embodiment of a system for quality assessment of medical images according to the present invention.

FIG. 5 shows a schematic diagram of another embodiment of a system for quality assessment of medical images according to the present invention. Said quality assessment system 1' comprises a processor 2 and a computer-readable storage medium 3, wherein the computer-readable storage medium 3 contains instructions for execution by the processor 2, wherein the instructions cause the processor 2 to perform the steps of the method disclose therein, e.g. the method disclosed in FIG. 4.

Imaging departments relying increasingly on KPIs in order to monitor and improve their performance can make use of the present invention, too. Such KPIs are typically related to quantities like equipment utilization, idle time, or patient throughput. In this context, the image data itself and its quality (e.g. in terms of compliance with planning guidelines, correctness and completeness of DICOM attributes) are thus addressed.

In summary, according to the present invention a technique for quality assessment and reporting is presented, which aims at enterprise image archives. It employs image processing techniques (like atlas based segmentation or classification based anatomy detection) in order to identify the visible anatomical structures. These information can be checked against the present DICOM information (e.g. Body Part Examined value or Anatomic Region Sequence code), and (if applicable) compared to scan planning guidelines. The proposed invention can be used as part of a PACS/VNA, or in the context of a dedicated (vendor independent) reporting solution.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A device for quality assessment of medical images, said device comprising:
    an image input configured to obtain a medical image acquired according to an imaging guideline,
    a converter configured to convert a textual description of the imaging guideline into a converted reference image;
    a database access unit configured to access a database storing reference images for a plurality of imaging guidelines and for obtaining a reference image based on the imaging guideline used for acquisition of the obtained medical image,
    an analysis unit configured to analyze the obtained medical image in view of at least one of the converted reference image, the obtained reference image or the used imaging guideline to generate quality information representing a quality of the obtained medical image based on, at least, an adherence to the used imaging guideline, and
    a quality output configured to output the generated quality information.

2. The device as claimed in claim 1, wherein said analysis unit is further configured to compare the obtained medical image with the reference image to generate quality information representing a level of similarity.

3. The device as claimed in claim 1, wherein said analysis unit is further configured to check compliance of the obtained medical image with the used imaging guideline to generate quality information representing compliance and/or the level of compliance.

4. The device as claimed in claim 1, wherein said analysis unit is further configured to use an imaging guideline including attributes, in particular DICOM attributes, and/or imaging planning guidelines in the analysis to generate said quality information representing compliance and/or the level of compliance of the obtained medical image with the attributes and/or imaging planning guidelines.

5. The device as claimed in claim 1, further comprising
an image processing unit configured to detect target anatomy and/or anatomical landmarks in the obtained medical image,
wherein said analysis unit is further configured to compare the detected target anatomy and/or anatomical landmarks in the obtained medical image with target anatomy and/or anatomical landmarks in the reference image to generate quality information representing a level of similarity.

6. The device as claimed in claim 1, further comprising
a registration unit configured to perform registration of the obtained medical image with the reference image,
wherein said analysis unit is configured to use the registered medical image in the analysis.

7. The device as claimed in claim 1, further comprising
an evaluation unit configured to evaluate the generated quality information of the quality assessment of a plurality of medical images to obtain an evaluation result,
wherein said output unit is further configured to output said evaluation result.

8. The device as claimed in claim 7, wherein said evaluation unit is further configured to generate guidance information indicating suggestions for improvement of future image acquisition.

9. The device as claimed in claim 1, wherein the converter is further configured to convert a textual description of the imaging guideline into standard text as used by a database linking standard text with reference images, wherein said database access unit is configured to retrieve a reference image from said database.

10. The device as claimed in claim 1, wherein said imaging guideline comprises one or more of an imaging protocol, an image acquisition protocol, scan planning guidelines, a DICOM protocol, clinical guidelines.

11. A method for quality assessment of medical images, said method comprising:
obtaining a medical image acquired according to an imaging guideline,
converting a textual description of the imaging guideline into a converted reference image;
accessing a database storing reference images for a plurality of imaging guidelines and for obtaining a reference image based on the imaging guideline used for acquisition of the obtained medical image,
analyzing the obtained medical image in view of at least one of the converted reference image, the obtained reference image or the used imaging guideline to generate quality information representing a quality of the obtained medical image based on, at least, an adherence to the used imaging guideline, and
outputting the generated quality information.

12. A system for quality assessment of medical images, said system comprising:
an image acquisition device configured to acquire medical images of a subject according to an imaging guideline, and
the device as claimed in claim 1 for quality assessment of medical images acquired with said imaging guideline.

13. A quality assessment system comprising a processor and a computer-readable storage medium, wherein the computer-readable storage medium contains instructions for execution by the processor, wherein the instructions cause the processor to perform the steps of:
obtaining a medical image acquired according to an imaging guideline,
converting a textual description of the imaging guideline into a converted reference image,
accessing a database storing reference images for a plurality of imaging guidelines and for obtaining a reference image based on the imaging guideline used for acquisition of the obtained medical image,
analyzing the obtained medical image in view of at least one of the converted reference image, the obtained reference image or the used imaging guideline to generate quality information representing a quality of the obtained medical image based on, at least, an adherence to the used imaging guideline, and
outputting the generated quality information.

14. A computer readable non-transitory medium having instructions stored thereon which, when carried out on a computer, cause the computer to perform the steps of the method as claimed in claim 11.

* * * * *